United States Patent
Chieh et al.

(10) Patent No.: US 10,139,396 B2
(45) Date of Patent: Nov. 27, 2018

(54) METHOD OF NONINVASIVELY DETECTING PLANT PATHOGENIC VIRUS AND ELECTRONIC APPARATUS THEREOF

(71) Applicant: NATIONAL TAIWAN NORMAL UNIVERSITY, Taipei (TW)

(72) Inventors: Jen-Jie Chieh, Taipei (TW); Yen-Hsiang Wang, Taipei (TW); Shien-Kuei Liaw, Taipei (TW); Wen-Chun Wei, Taipei (TW); Ming-Hsien Chiang, Taipei (TW)

(73) Assignee: NATIONAL TAIWAN NORMAL UNIVERSITY, Taipei (TW)

( * ) Notice: Subject to any disclaimer, the term of this patent is extended or adjusted under 35 U.S.C. 154(b) by 142 days.

(21) Appl. No.: 15/096,292

(22) Filed: Apr. 12, 2016

(65) Prior Publication Data

US 2016/0298161 A1 Oct. 13, 2016

(30) Foreign Application Priority Data

Apr. 13, 2015 (TW) .............................. 104111800 A

(51) Int. Cl.
*G01N 21/64* (2006.01)
*C12Q 1/02* (2006.01)
(Continued)

(52) U.S. Cl.
CPC ........ *G01N 33/5097* (2013.01); *G01J 3/4406* (2013.01); *G01N 21/6486* (2013.01);
(Continued)

(58) Field of Classification Search
CPC .......... G01J 3/4406; G01N 2021/6421; G01N 2021/6484; G01N 2021/8466;
(Continued)

(56) References Cited

U.S. PATENT DOCUMENTS

| 2004/0029208 A1* | 2/2004 | Ravn ..................... G01N 33/50 435/29 |
| 2004/0233448 A1* | 11/2004 | Goulas ............... G01N 21/3151 356/432 |
| 2010/0111369 A1* | 5/2010 | Lussier .................... G01J 3/02 382/110 |

FOREIGN PATENT DOCUMENTS

| CN | 101625314 | 1/2010 |
| CN | 101715551 | 5/2010 |

(Continued)

OTHER PUBLICATIONS

Chaerle et al. Journal of Plant Physiology, vol. 164, 2007, pp. 253-262.*

(Continued)

*Primary Examiner* — Maureen Wallenhorst
(74) *Attorney, Agent, or Firm* — JCIPRNET

(57) ABSTRACT

A method of noninvasively detecting plant pathogenic virus and an electronic apparatus thereof are provided. The method is adapted to the electronic apparatus for detecting pathogenic virus in plants. The method includes the following steps. An excitation light beam is projected to the plant, and a reaction light emitted by the plant in response to the excitation light is received. An analytic optical spectrum corresponding to the reaction light is obtained, and whether the plant has the pathogenic virus or not is determined according to the analytic optical spectrum.

6 Claims, 3 Drawing Sheets

(51) Int. Cl.
*G01N 33/50* (2006.01)
*G01J 3/44* (2006.01)
*G01N 21/84* (2006.01)

(52) U.S. Cl.
CPC ....... *C12Q 1/02* (2013.01); *G01N 2021/6421* (2013.01); *G01N 2021/6484* (2013.01); *G01N 2021/8466* (2013.01); *G01N 2201/06113* (2013.01); *G01N 2333/08* (2013.01)

(58) Field of Classification Search
CPC ............... G01N 21/64; G01N 21/6486; G01N 2201/06113; G01N 2333/08; G01N 33/5097; C12Q 1/02
USPC ......... 436/164, 172; 435/5, 235.1, 239, 410; 422/82.05, 82.08, 82.09
See application file for complete search history.

(56) References Cited

FOREIGN PATENT DOCUMENTS

| | | | |
|---|---|---|---|
| CN | 102348976 | | 2/2012 |
| CN | 102405405 | | 4/2012 |
| JP | 2013-36889 | * | 2/2013 |
| TW | I424145 | | 1/2014 |
| TW | 201407150 | | 2/2014 |
| WO | 2007021485 | | 2/2007 |

OTHER PUBLICATIONS

Eun et al. Journal of Virological Methods, vol. 87, 2000, pp. 151-160.*

* cited by examiner

METHOD OF NONINVASIVELY DETECTING PLANT PATHOGENIC VIRUS AND ELECTRONIC APPARATUS THEREOF

CROSS-REFERENCE TO RELATED APPLICATION

This application claims the priority benefit of Taiwan application serial no. 104111800, filed on Apr. 13, 2015. The entirety of the above-mentioned patent application is hereby incorporated by reference herein and made a part of this specification.

BACKGROUND OF THE INVENTION

1. Field of the Invention

The present invention generally relates to detecting method and electronic apparatus with the method, in particular, to a method of noninvasively detecting plant pathogenic virus and an electronic apparatus with the method.

2. Description of Related Art

With the development of biotechnology and cultivation facilities, the floral industry is now having been a floriculture industry with high economic value. A typical flower in the floral industry is orchid. Due to a very high ornamental value for orchid, it has been widely cultivated and planted, and has been greatly used in various occasions of horticulture landscaping, welcome banquet, and so on.

During the process of cultivating orchid, in addition to appropriate fertilization, irrigation and environmental regulation, the prevention of viruses and pest is also extremely important. A lot of types of viruses can affect orchid, of which several viruses would cause the change in appearance of orchid and resulting in the affection on the ornamental value and selling appearance. Therefore, the orchid plants having been infected by foregoing virus need to be early detected and applied with treatment or impose isolation, thereby avoiding a single infected orchid plant to expand its influence to other neighboring orchid plants.

However, the current virus detection method is generally performed on the orchid specimen by test strip or biochemical testing. Taking an example, the juice printed from the orchid leaves is mixed with the ELISA (Enzyme-Linked ImmunoSorbent Assay) detection reagent, and the virus detection is performed by the ELISA detector. In another example, a specific test strip is used to detect the orchid specimen and determine whether or not a virus infection occurs. However, the orchid specimen collection would inevitably cause a wound on orchid and, contrarily, increase the risk of future infections by virus on orchid. In the matter, how to provide a method of noninvasively detecting plant pathogenic virus is still one of the goals in effort for those with skill in the art.

SUMMARY OF THE INVENTION

The present invention provides a method of noninvasively detecting plant pathogenic virus and an electronic apparatus thereof, in which the pathogenic virus of the plant can be precisely detected at the situation without causing a wound.

An embodiment of the invention provides a method of noninvasively detecting plant pathogenic virus, adapted to an electronic apparatus to detect a plant. The method of noninvasively detecting plant pathogenic virus comprises the following steps: projecting an excitation light beam onto the plant; receiving a reaction light emitted by the plant in response to the excitation light beam; obtaining an analytic optical spectrum corresponding to the reaction light; and determining whether the plant has a pathogenic virus or not according to the analytic optical spectrum.

Another embodiment of the invention provides an electronic apparatus, used to detect a plant. The electronic apparatus comprises an excitation light source, a light transceiver, a spectrometer, and a processing unit. The excitation light source provides an excitation light beam. The light transceiver projects the excitation light beam onto the plant and receives a reaction light emitted by the plant in response to the excitation light beam. The spectrometer is coupled to the light transceiver, and the spectrometer obtains an analytic optical spectrum corresponding to the reaction light. The processing unit is coupled to the spectrometer. The processing unit determines whether the plant has a pathogenic virus or not according to the analytic optical spectrum.

As to the foregoing descriptions, in the method of noninvasively detecting plant pathogenic virus and the electronic apparatus with the method, as provided in the invention, the analytic optical spectrum is obtained by projecting the excitation light beam onto the plant and whether the plant has a pathogenic virus or not is determined according to the analytic optical spectrum. The foresaid method of detecting plant pathogenic virus does not cause the wound of plant, and therefore is a method of noninvasively detecting plant pathogenic virus. In other words, the method of detecting plant pathogenic virus as proposed by the application can precisely determine whether the plant has been infected by pathogenic virus or not, but also reduce wound on the plant caused by collection of plant specimen and avoid future infection by virus.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
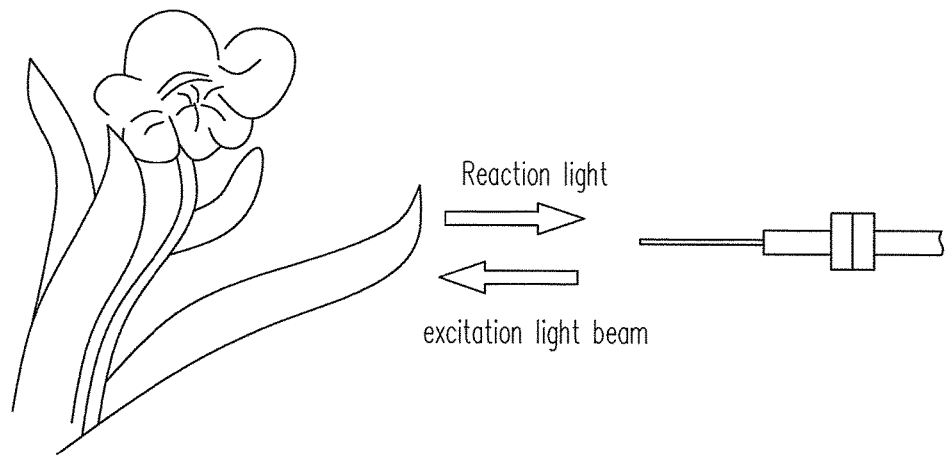
FIG. 1 is a drawing, schematically illustrating a method of detecting plant pathogenic virus, according to an embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

The method of detecting plant pathogenic virus and the electronic apparatus as provided in the invention are suitable for detecting the virus in orchid, but are not limited thereto. In better detail, the number of viruses capable of infecting the orchid has been 24 or more. However, the viruses of Cymbidium Mosaic Virus (CyMV) and Odontoglossum Ringspot Virus (ORSV) in those viruses are easily causing the change in appearance of orchid, such as withered leaves or yellow leaves, so the ornamental value for the orchid is reduced. Therefore, in several embodiments of the invention, the method of detecting plant pathogenic virus and the electronic apparatus thereof are taking the CyMV and ORSV as the detecting targets. However, remarkably, the detection object and detection target for the method of detecting plant pathogenic virus and the electronic apparatus are not limited to those above.

FIG. 1 is a drawing, schematically illustrating a method of detecting plant pathogenic virus, according to an embodiment of the present invention. Referring to FIG. 1, when an excitation light beam is projected onto the orchid, if the orchid carries CyMV, ORSV, or both, then the CyMV and ORSV produce the fluorescent lights respectively in response to the excitations of the excitation light beam respectively on CyMV and ORSV. At this moment, if the fluorescent lights can be detected and the wave band and the light intensity of the fluorescent lights can be analyzed by use of spectrometer, then the infection status and the degree of infection for the orchid can be determined. In other words, the method of detecting plant pathogenic virus as proposed by the application can determine whether or not the plant has been infected by CyMV and ORSV without harming the orchid. In addition, the identification in semi-quantitative concentration for those two viruses can be done according to the light intensity of the fluorescent.

Figure 2:
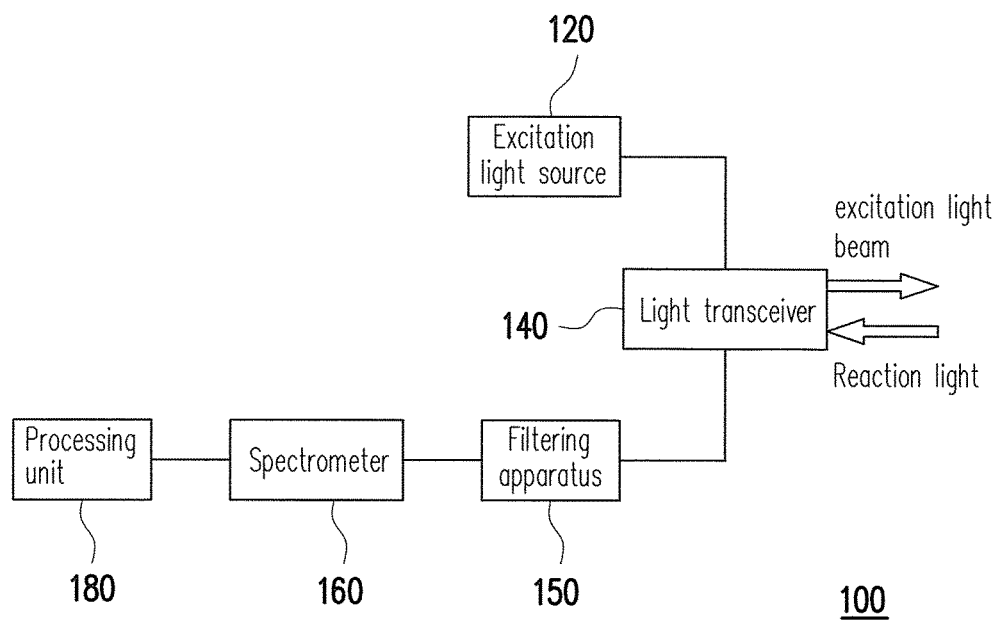
FIG. 2 is a drawing, schematically illustrating the block diagram of an electronic apparatus, according to an embodiment of the present invention.

FIG. 2 is a drawing, schematically illustrating the block diagram of an electronic apparatus, according to an embodiment of the present invention. Referring to FIG. 2, the electronic apparatus 100 includes an excitation light source 120, a light transceiver 140, a spectrometer 160, and a processing unit 180. The excitation light source 120 can be a laser light source as an example, and the excitation light beam provided from the excitation light source 120 can be the laser light beam. In better detail, the excitation light source 120 includes a laser diode or multiple laser diodes arranged in an array, but is not limited thereto.

The light transceiver 140 in an example can be a coupler with probe for emitting and receiving light. The light transceiver 140 is coupled to the excitation light source 120, and projects the excitation light beam onto the target by the probe. On the other hand, by the probe, the light transceiver 140 also receives the reaction light emitted from the target in response to the excitation light beam. In an embodiment, the reaction light in an example can be fluorescent light or phosphorescent light. The foresaid target in an example can be plant specimen, animal specimen, pathogen target, and so on, but is not limited thereto.

The spectrometer 160 is coupled to the light transceiver 140, to obtain the analytic optical spectrum of the foresaid reaction light. In better detail, the spectrometer 160 usually has a charged-coupled device (CCD), which can detect the reaction light at several wavelength parts via multiple optical devices as being implemented, and thereby obtain the analytic optical spectrum. Remarkably, the excitation light source 120, the light transceiver 140 and the spectrometer 160 in an example can be coupled to each other through line tubes, so to transmit the excitation light beam and the reaction light. In an embodiment of the invention, a filtering apparatus 150 is coupled between the light transceiver 140 and the spectrometer 160 to filter out a wave component in part of the reaction light and avoid the affection from nose.

The processing unit 180 in an example can be a central processing unit (CPU), or the other of programmable microprocessor, digital signal processor (DSP), programmable controller, application specific integrated circuits (ASIC), or programmable logic device (PLD), but is not limited thereto. In an embodiment, the processing unit 180 is coupled to the spectrometer 160, to receive the analytic optical spectrum as obtained by the spectrometer and analyze the analytic optical spectrum.

Remarkably, in an embodiment of the invention, the electronic apparatus 100 can further include devices such as storage unit and so on (not shown). The storage unit in an example can be any type of hard disk drive (HHD), random access memory (RAM), read-only memory (ROM), flash memory, or any combination thereof, but is not limited thereto.

The electronic apparatus 100 can be the electronic apparatus dedicated to plant pathogen detection or can be the electronic apparatus which integrates plant pathogen detection and other existing functions in one apparatus. For example, the electronic apparatus 100 can be asset-top box of Multimedia On Demand (MOD), which also has the function to detect the plant pathogen virus.

Figure 3:
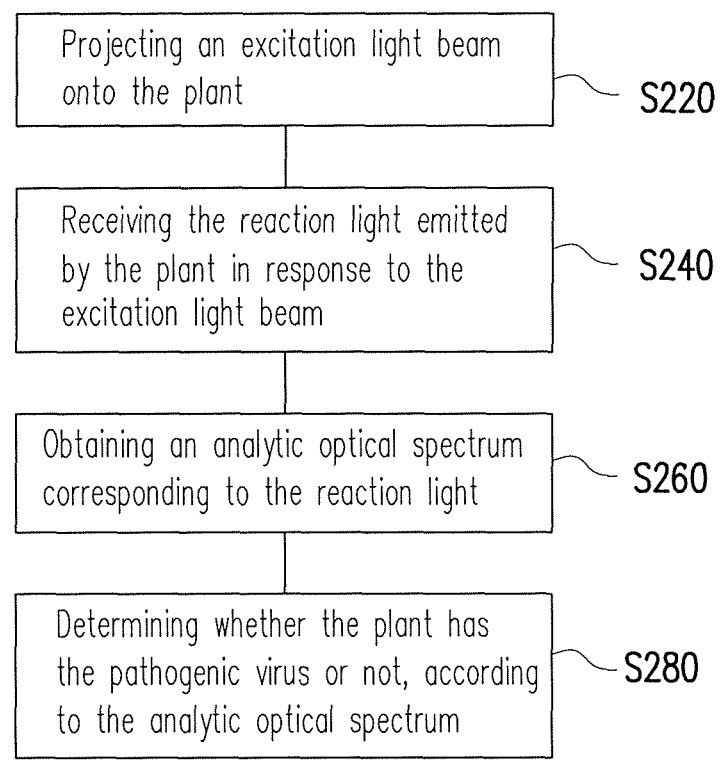
FIG. 3 is a drawing, schematically illustrating the flow diagram of the method of detecting plant pathogenic virus, according to an embodiment of the present invention.

FIG. 3 is a drawing, schematically illustrating the flow diagram of the method of detecting plant pathogenic virus, according to an embodiment of the present invention. The method of detecting plant pathogenic virus as proposed in an embodiment of the invention is a method of noninvasively detecting plant pathogenic virus. The method of detecting plant pathogenic virus can be adapted to the electronic apparatus as described in FIG. 2 but is not limited thereto. Referring to FIG. 2 and FIG. 3, in the method of detecting plant pathogenic virus, an excitation light beam is projected onto the plant (step S220). In the embodiment, the excitation light beam as provided by the excitation light source 120 can be projected onto the root, the leaf or the stem of orchid as an example. By use of the probe of the light transceiver 140, the excitation light beam can be concentrated into a small range to project onto the plant. Thereby, the excitation light beam can be selectively projected, as needed for detection, onto any location of the orchid, so to detect whether or not the detected location of the orchid has been infected by CyMV and ORSV. Remarkably, in order to excite the CyMV and ORSV in better performance, the excitation light beam provided by the excitation light source 120 in an example can be a laser beam matching to the visible light band, particularly to green light band.

Further, the light transceiver 140 can also use the probe to receive the reaction light emitted by the orchid in response to the excitation light beam (step S240), and the reaction light is transmitted to spectrometer 160 through the line tube. In an embodiment of the invention, a filtering apparatus 150 is also implemented between the light transceiver 140 and the spectrometer 160. The filtering apparatus 150 filters out a wave component in part of the reaction light. The wave range of the wave component in part is 0 nm to 550 nm.

The spectrometer 160 receives the reaction light and obtains an analytic optical spectrum corresponding to the reaction light (step S260). In an embodiment, the analytic optical spectrum obtained by the spectrometer 160 has a range of 488 nm to 1140 nm, which is mainly corresponding to the visible light band. The processor 180 obtains the analytic optical spectrum and determines whether the plant has the pathogenic virus or not, according to the analytic optical spectrum (step S280).

Figure 4:
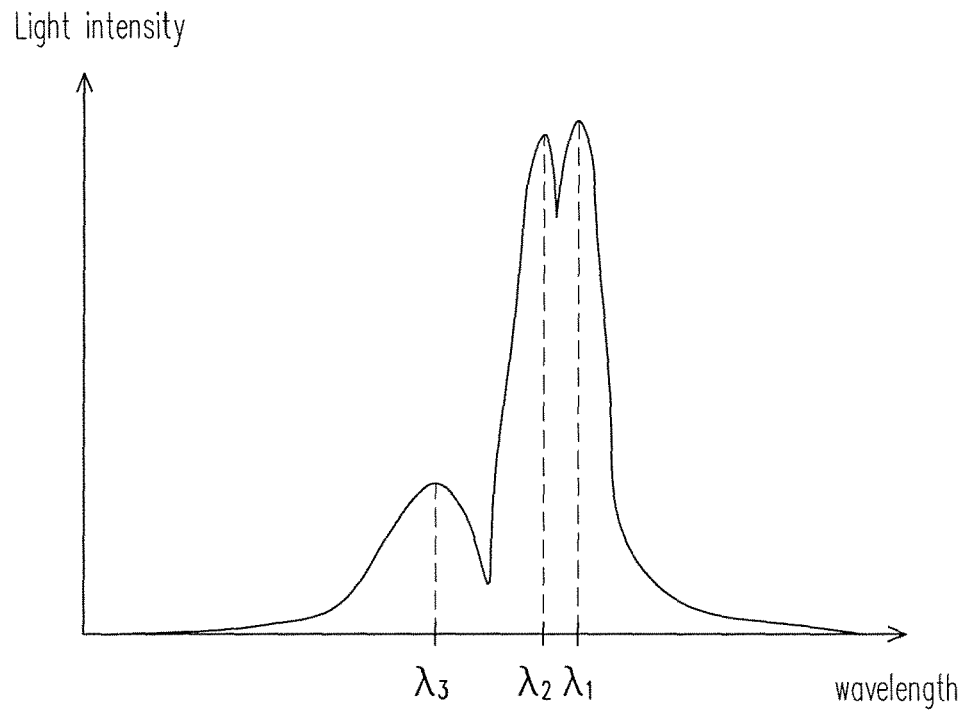
FIG. 4 is a drawing, schematically illustrating the spectrum of pathogenic virus, according to an embodiment of the present invention.

In better detail, a specific manner to determine whether the orchid is infected by CyMV and ORSV based on the analytic optical spectrum is comparing the analytic optical spectrum with the spectrum of CyMV and ORSV. FIG. 4 is a drawing, schematically illustrating the spectrum of pathogenic virus, according to an embodiment of the present invention. In better detail, FIG. 4 is a complex spectrum of pathogenic virus from the CyMV and the ORSV. Referring to FIG. 4, when the ORSV is illuminated by the foresaid excitation light beam, the fluorescent light emitted by ORSV has at least one wavelength component with relatively strong peak value within the first weave band $\lambda_1$. On the other hand, when the CyMV is illuminated by the foresaid excitation light beam, the fluorescent light emitted by CyMV has multiple wavelength components with relatively strong peak values within the second weave band $\lambda_2$ and the third weave band $\lambda_3$. Remarkable, the first wave band $\lambda_1$ and the second weave band $\lambda_2$ are located within the infrared wavelength range and the third weave band $\lambda_3$ is located within the yellow wavelength range. Therefore, if the fluorescent wavelength band with relative strong peak value in the analytic optical spectrum can be detected, then it can be accordingly confirmed that the orchid has been infected by the CyMV and the ORSV.

Figure 5:
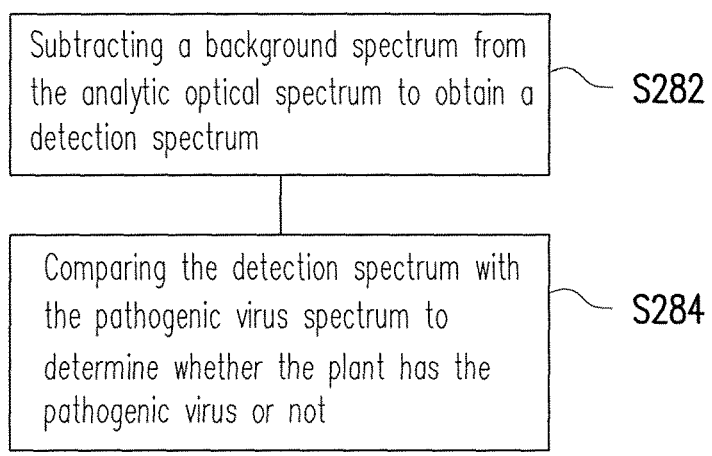
FIG. 5 is a drawing, schematically illustrating the flow diagram for determining whether or not the plant has been infected by pathogenic virus, according to an embodiment of the present invention.

FIG. 5 is a drawing, schematically illustrating the flow diagram for determining whether or not the plant has been infected by pathogenic virus, according to an embodiment of the present invention. Referring to FIGS. 2-5, the processing unit 180 first subtracts a background spectrum from the analytic optical spectrum to obtain a detection spectrum (S282). In detail, when the orchid is illuminated by the excitation light beam, the substance itself of cell, chlorophyll, and so on would also be excited to generate fluorescent light. Therefore, to avoid the situation that the precision of the method of detecting plant pathogenic virus is affected by the fluorescent light from the foresaid substance, the background spectrum corresponding to the foresaid substance is necessary to be firstly subtracted. A method to obtain the background spectrum in an example is projecting the excitation light beam onto the orchid without being infected to generate the reaction light, from which the background spectrum is obtained. Remarkably, the background spectrum for each location of orchid, such as root, leaf and stem is not always the same, and needs to be respectively obtained.

After obtaining the detection spectrum, the processing unit 180 compares the detection spectrum with the pathogenic virus spectrum to determine whether the plant has the pathogenic virus or not (step S284). In better detail, the processing unit 180 is comparing the light intensities in the detection spectrum and in the pathogenic virus spectrum at the at least one specific wavelength band. According to the comparing result, it is determined whether the plant carries the pathogenic virus or not. In an embodiment, the specific wavelength band is the first wave band $\lambda_1$, the second weave band $\lambda_2$, and the third weave band $\lambda_3$ as stated in FIG. 4. In detail, the processing unit 180 determines whether the orchid has the CyMV and ORSV according to the light intensities of the detection spectrum at the first wave band $\lambda_1$, the second weave band $\lambda_2$, and the third weave band $\lambda_3$.

In an embodiment of the invention, when the light intensities of the detection spectrum at the first wave band $\lambda_1$, the second weave band $\lambda_2$, and the third weave band $\lambda_3$ are respectively over the corresponding threshold values, then it is determined that the orchid has been infected by the CyMV and ORSV. In another embodiment of the invention, when the light intensities of the detection spectrum at the first wave band $\lambda_1$, the second weave band $\lambda_2$, and the third weave band $\lambda_3$ are matching to the light intensities of the pathogenic virus spectrum at the first wave band $\lambda_1$, the second weave band $\lambda_2$, and the third weave band $\lambda_3$, it is determined that the orchid has been infected by the CyMV and ORSV. Remarkably, the comparing manner between the detection spectrum and the pathogenic virus spectrum is not limited to the above manner.

The foresaid background spectrum and pathogenic virus spectrum can be stored in the storage unit of the electronic apparatus 100. The processing unit 180 further reads the corresponding background spectrum and the corresponding pathogenic virus spectrum from the storage unit after obtaining the analytic optical spectrum of orchid, so to determine whether the orchid has been infected by the CyMV and ORSV or not.

As to the foregoing descriptions, the method of noninvasively detecting plant pathogenic virus and the electronic apparatus provided by the invention can obtain the analytic optical spectrum by projecting the excitation light beam onto the orchid (plant) and determine whether the orchid has the pathogenic virus or not according to the analytic optical spectrum. In better detail, the pathogenic virus includes CyMV and ORSV. The CyMV and ORSV, after illuminating by the excitation light beam, would correspondingly generate fluorescent light. In the analytic optical spectrum, it can be determined whether the orchid has been infected by CyMV and ORSV or not, according to the light intensity at the specific fluorescent wavelength band, corresponding to CyMV and ORSV. Even further, the relative concentration of the foresaid pathogenic virus can be determined. The foresaid method of detecting plant pathogenic virus does not wound the orchid and therefore is the method of noninvasively detecting plant pathogenic virus. In other words, the method of detecting plant pathogenic virus as proposed by the application can precisely determine whether the plant has been infected by pathogenic virus or not, but also reduce wound on the plant caused by collection of plant specimen and avoid future infection by virus.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:
1. An electronic apparatus, configured to detect a plant, the electronic apparatus consisting of:
   an excitation light source, providing an excitation light beam;
   a light transceiver coupled to the excitation light source, wherein the light transceiver comprises a probe end having a needle-like structure configured to both project and concentrate the excitation light beam directly onto a location of the plant and to receive a reaction light beam emitted directly by the plant through the probe end in response to the excitation light beam, wherein the excitation light beam and the reaction light beam are configured to not cause an invasive damage to the plant;
   a spectrometer, coupled to the light transceiver, the spectrometer configured to obtain an analytic optical spectrum corresponding to the reaction light beam;

a filtering apparatus, coupled between the light transceiver and the spectrometer, the filtering apparatus configured to filter out a wave component in part of the reaction light beam; and a processing unit, coupled to the spectrometer, the processing unit configured to determine whether the plant has a pathogenic virus or not according to the analytic optical spectrum.

2. The electronic apparatus as recited in claim 1, wherein the processing unit is further configured to subtract a background spectrum from the analytic optical spectrum to obtain a detection spectrum, and compares the detection spectrum with a pathogenic virus spectrum to determine whether the plant has the pathogenic virus or not, wherein the background spectrum is reflection light from a reference plant that is not infected with the pathogenic virus.

3. The electronic apparatus as recited in claim 2, wherein the processing unit is further configured to compare light intensities of at least one specific wave band in the detection spectrum and the pathogenic virus spectrum, and determine whether the plant has the pathogenic virus or not according to at least one comparing result of the light intensities of the at least one specific wave band.

4. The electronic apparatus as recited in claim 1, wherein a wave range of the wave component in part is 0 nm to 550 nm.

5. The electronic apparatus as recited in claim 1, wherein the excitation light beam projected by the excitation light source is projected onto a root, a leaf or a stern of the plant.

6. The electronic apparatus as recited in claim 1, wherein the plant is an orchid, and the pathogenic virus comprises Cymbidium Mosaic Virus (CyMV) and Odontoglossum Ringspot Virus (ORSV).

\* \* \* \* \*